(12) United States Patent
Takahashi et al.

(10) Patent No.: US 7,029,881 B1
(45) Date of Patent: Apr. 18, 2006

(54) METHODS FOR CONSTRUCTING DNA LIBRARY AND SUPPORT CARRYING DNA LIBRARY IMMOBILIZED THEREON

(75) Inventors: Kojiro Takahashi, Hiroshima-ken (JP); Osamu Takai, Hiroshima-ken (JP); Michifumi Tanga, Yamaguchi-ken (JP)

(73) Assignees: Nihon Parkerizing Hiroshima Co., Ltd., Hiroshima-ken (JP); Toyo Kohan Co., Ltd., Tokyo (JP)

( * ) Notice: Subject to any disclaimer, the term of this patent is extended or adjusted under 35 U.S.C. 154(b) by 0 days.

(21) Appl. No.: 10/030,619

(22) PCT Filed: May 10, 2000

(86) PCT No.: PCT/JP00/03000

§ 371 (c)(1),
(2), (4) Date: Oct. 21, 2002

(87) PCT Pub. No.: WO00/68368

PCT Pub. Date: Nov. 16, 2000

(30) Foreign Application Priority Data

May 10, 1999 (JP) ................................. 11/127943

(51) Int. Cl.
*C12P 19/36* (2006.01)
(52) U.S. Cl. ................ 435/91.1; 435/6; 435/5; 435/4; 435/91.2; 435/91.51; 435/DIG. 49; 435/DIG. 46; 536/23.1; 536/24.1; 536/24.2
(58) Field of Classification Search .............. 435/6, 435/91.1, 91.2, 91.52, 283.1, 287.2, 288.4, 435/DIG. 22, DIG. 46; 536/23.1, 24.1, 24.2
See application file for complete search history.

(56) References Cited

U.S. PATENT DOCUMENTS

| 5,656,462 A | * | 8/1997 | Keller et al. ............... 435/91.2 |
| 6,225,077 B1 | * | 5/2001 | Schmidt et al. ............... 435/19 |
| 6,489,111 B1 | * | 12/2002 | Takahashi et al. ............. 435/6 |

FOREIGN PATENT DOCUMENTS

| EP | 0 701 001 A2 | 3/1996 |
| WO | WO 99/63072 A1 | 12/1999 |
| WO | WO 99/41362 A1 | 11/2000 |

OTHER PUBLICATIONS

Schena, M. et al. "Parallel Human Genome Analysis: Microarray-beased expression Monitoring of 1,000 Genes," Proc. Natl. Acad. Sci. USA (1996) vol. 93, P. 10614-10619 Schena, M. et al.

* cited by examiner

*Primary Examiner*—T. D. Wessendorf
(74) *Attorney, Agent, or Firm*—Browdy and Neimark, PLLC (57) ABSTRACT

Method and apparatus for constructing a cDNA library by hybridizing mRNA with oligo (dT) on a support and treating with a reverse transcriptase to immobilized complementary DNA, or for constructing a gDNA library by ligating a double-stranded chromosomal DNA library with an oligonucleotide on a support having a restriction enzyme site and then immobilizing the gDNA library.

4 Claims, 8 Drawing Sheets

Support (T1)

US 7,029,881 B1

METHODS FOR CONSTRUCTING DNA LIBRARY AND SUPPORT CARRYING DNA LIBRARY IMMOBILIZED THEREON

REFERENCE TO RELATED APPLICATIONS

The present application is the national stage under 35 U.S.C. 371 of international application PCT/JP00/03000, filed May 10, 2000, which designated the United States, and which application was not published in the English language.

FIELD OF THE INVENTION

The present invention relates to molecular biology and biochemical gene technology, protein technology, and cell technology. More particularly, the present invention relates to a method for construction of a plurality of supports on which a DNA library is immobilized using a micro amount of DNA test material, a method for constructing the supports, and supports on which DNA is immobilized.

BACKGROUND OF THE INVENTION

DNA is a very important test material. In conventional methods for working with DNA, DNA is amplified using a Polymerase Chain Reaction (hereinafter, PCR) and divided to small groups. The DNA test material is preserved at remarkably low temperatures in a freezer. Conventionally, a DNA library is produced in a solution so that a replica of the DNA library cannot be produced. Accordingly, one must work very carefully with a DNA library in solution obtained from tissue or cells in order to search and identify the genes therein.

One purpose of the present invention is to provide a method for constructing a DNA library support, i.e., an original support, on which A DNA library is immobilized using a micro amount of the DNA library test material. Another purpose of the present invention is to provide a method for constructing the necessary number of replica supports. Furthermore, another purpose of the present invention is to provide a support on which a replica of DNA is immobilized.

SUMMARY OF THE INVENTION

The method for constructing a cDNA (complementary DNA) library according to the present invention comprises, hybridizing oligo $(dT)_n$ on a support, and thereafter messenger RNA (hereinafter, mRNA), and reacting it with reverse transcriptase (hereinafter, RT) in order to immobilize complementary DNA.

In a method for constructing a cDNA library according to the present invention, mRNA is dehybridized from a cDNA library immobilized on a support. The method comprises immobilizing the same cDNA library by using dehybridized mRNA.

In a method for constructing a genomic DNA (hereinafter, gDNA) library according to the present invention, a double stranded gDNA is ligated to an oligo nucleotide on a support with restrictive enzyme portion.

A single stranded gDNA library according to the present invention is produced by ligating double stranded gDNA with respect to an oligonucleotide on a support having a restrictive enzyme portion which ligates the double stranded gDNA.

Another method for a single stranded gDNA library according to the present invention comprises dehybridizing an anti-sense portion of the gDNA library obtained above, and synthetically immobilizing a sense portion of the gDNA on a support using the anti-sense portion.

In any of the processes according to the present invention the support has been previously chemically modified with a nucleotide or an oligo nucleotide.

The substrate of the present invention comprises a support on which a DNA library is immobilized by any one of the methods described above. In another embodiment of the present invention, a single stranded DNA library is immobilized.

DETAILED DESCRIPTION OF THE INVENTION

A chemically modified original support which has been chemically modified with respect only to a nucleotide or oligonucleotide and a plurality of supports for producing replicas are prepared so as to produce an original support and replica supports. The supports are introduced into a replica constructing device.

Figure 1:
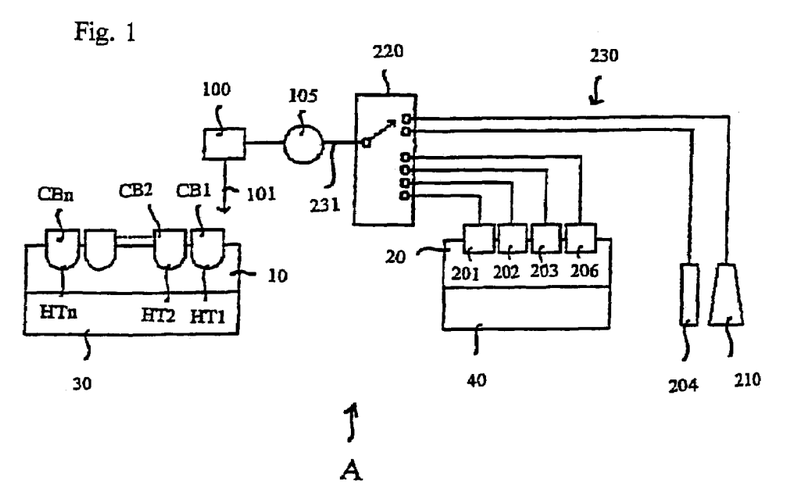
FIG. 1 is a schematic view of a device for constructing a cDNA library support according to the present invention.
Figure 2:
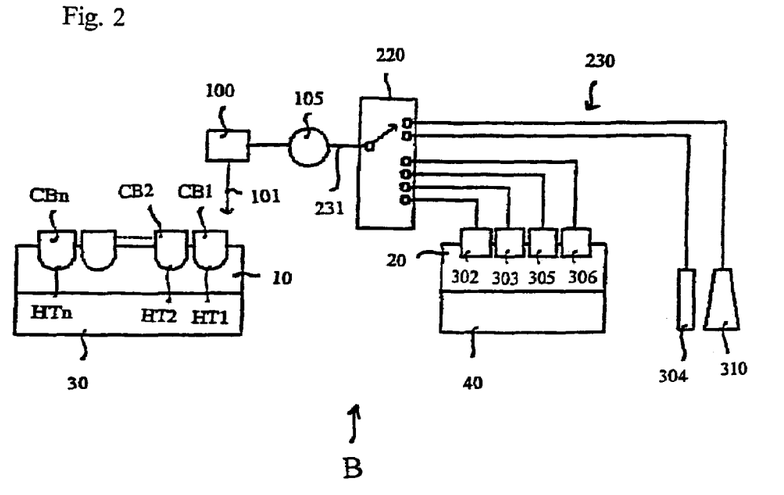
FIG. 2 is a schematic view of a device for constructing a gDNA library according to the present invention.
Figure 3:
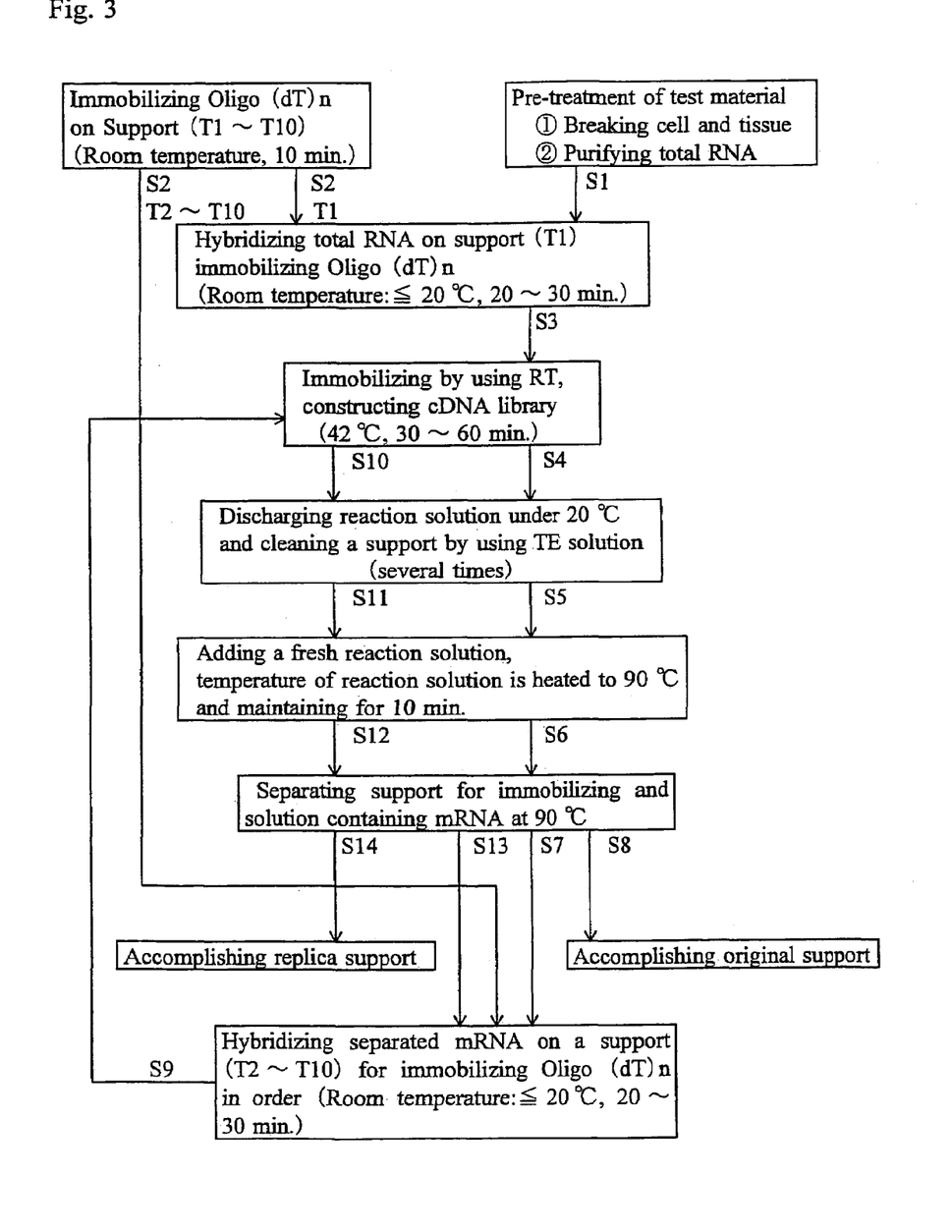
FIG. 3 is a flow chart for explaining a process for constructing a cDNA library support according to the present invention.
Figure 5:
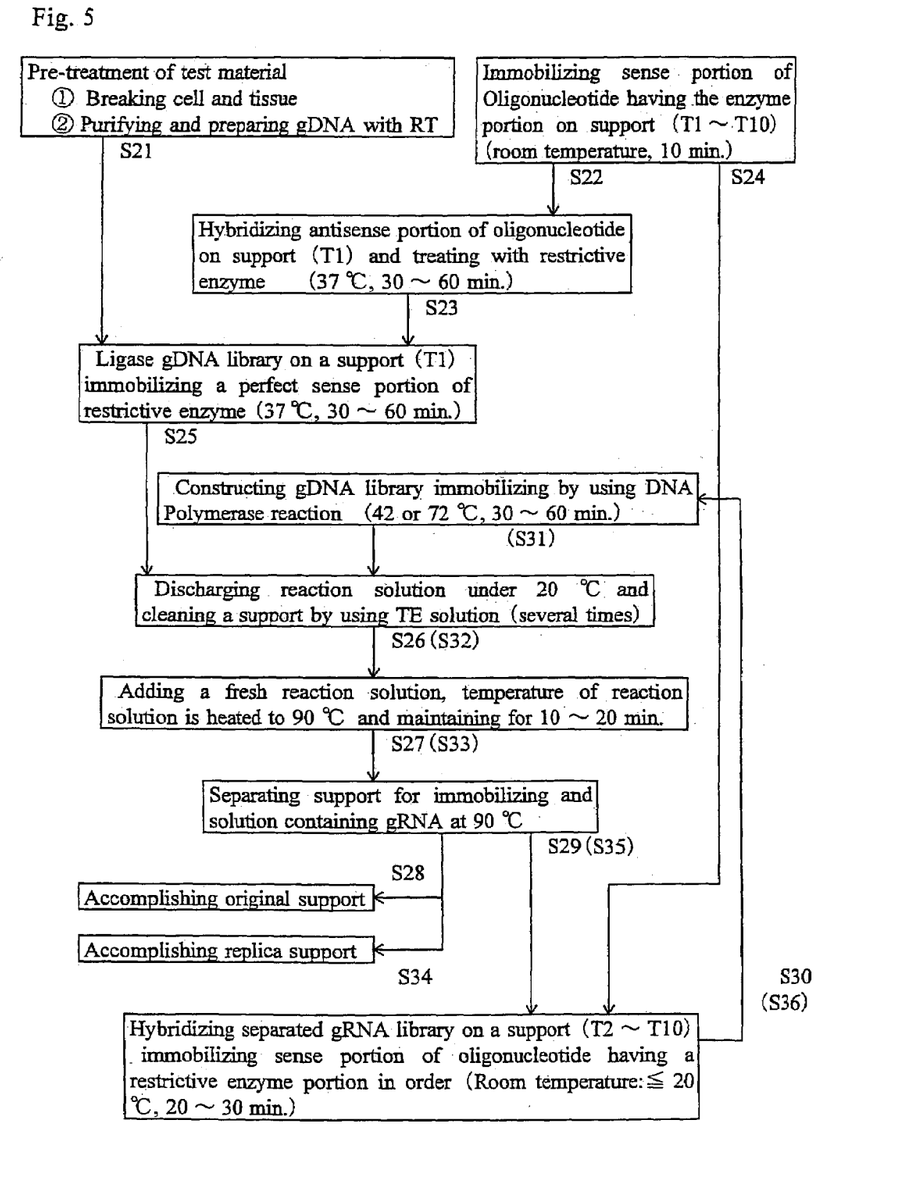
FIG. 5 is a flow chart for explaining a process of constructing a gDNA library support according to the present invention.

A device for constructing a DNA library support according to the present invention will be explained with reference to the drawings. FIG. 1 is a schematic view of a device for constructing a cDNA library support. FIG. 2 is a schematic view of a device for constructing a cDNA library support. FIG. 3 is a flow chart explaining a process of constructing a cDNA library support. FIG. 5 is a flow chart for explaining a gDNA library support.

FIG. 1 is a schematic view of a device for automatically constructing and duplicating a cDNA library support. A device for constructing a DNA library support as shown in FIG. 1 comprises liquid feeding means 105 for feeding reaction solution to a container, a liquid feeding switch means 220 for stopping the flow of reaction solution and feeding new reaction solution, nozzle driving means 100 for driving a nozzle 101 for inleting/outleting test material in a front-rear and right-left direction in a plane and an upper-lower direction, solution temperature controlling means 30 for heating or cooling the reaction solution in the container, test material container holding means 20 for holding containers into which each test material or solution is set for constructing respective immobilized DNA library supports, and test material control means for maintaining the test material container holding means at a predetermined temperature, etc. It is preferable that the container holding means 10 hold 96 or more test material containers to be connected to a PCR device and/or a PCR analysis device for subsequent use. It is preferable that the test material container holding means comprise at least four test material container inserting holes for replica supports. It is preferable that the number of container inserting holes provided at the test material container holding means 20 be ten holes or more, for subsequent connection to the PCR device and/or the PCR product analysis device. It is preferable that the container holding means 10 and the test material container holding means 20 be an aluminum block with good conductivity for thermally controlling the solution temperature controlling means 30 and the test material container temperature control means 40.

It is preferable that a support for construction a DNA library support be a plate shape, a ball shape, a cube shape or a grain shape in the both the original support and replica supports. Although the material of which the support is made is not specified, it is preferable that the material not react with reaction solution or that the material does not deposit harmful material when exposed to a DNA immobilization reaction. For example, plastic, glass, silicon, and metals are preferred materials. A plate shape, a ball shape, a cube shape and on the like are preferred. Particularly, a support made of diamond or carbon atoms including diamond is preferred.

Production of Original Support and its Replica Support with cDNA Library

Referring to FIGS. 1 and 3, a process for constructing an original support and replica supports on which a cDNA library is immobilized and its will be explained. First, a necessary number (T1–Tn) of supports of 3 mm×3 mm×0.1 mm chemically modified with respect only to (dT)n, are prepared before a DNA library is immobilized on these supports. A supports modified with oligo (dT)n and is used because it is easy to hybridize mRNA in total RNA that has been chemically modified. These supports are inserted into containers CB1 to CBn and the containers are set into the container holding means 10. In such a case, it is preferable to insert one support into a first container in view of constructing an original support as an immobilized cDNA library and its replica support using a micro amount of mRNA obtained from a small amount of test material. Regarding an order of setting containers CB1–CBn into which a chemically modified support is inserted at the container holding means, the container CB1 an original support in which a chemically modified is set is inserted into a first inserting portion HT1. The necessary number of containers (CB2–CBn) for replica supports into which the corresponding number of chemically modified supports (T2–Tn) is set, respectively, are inserted into a second inserting hole HT2, . . . to the $n^{th}$ inserting hole HTn in order.

Production of Original Support

Reaction solution 203, which includes purified total RNA solution 201, RT enzyme solution 202 and nucleotide (dT, dA, dG, dC) is set into the test material container holding means 20 controlled at a predetermined temperature (i.e., 4° C.). Tris ethylene diamine tetraacetic acid (hereinafter, TE) solution 204 for cleaning/eluting DNA (buffer solution including TE) and a waste solution tank 210 and others are provided. A capillary tube 230 is provided as a liquid feeding path by connection to the liquid feeding switch means 220 for feeding the respective solution. It is preferred that the capillary tube 230 be a corrosion resistant stainless tube for liquid chromatography. It is preferred that the connection between the test material inlet nozzle 101 and the liquid feeding switch means 220 through the liquid feeding means 105 be a silicone tube 231. Then the test material inlet nozzle 101 is moved to a position of the hole HT1 in the container holding means 10 so as to insert the nozzle 101 into the container CB1 in which the first support (T1) is set. The liquid feeding switch means 220 is provided at a side of the reaction solution, and the reaction solution is fed to the container CB1 by driving the liquid feeding means 105. The liquid feeding switch means 220 is shifted to the total RNA solution 201 and the predetermined amount of the solution 201 is inleted by the liquid feeding means 105. After passing a predetermined time (for example, 20 to 30 minutes) at a temperature equal to or lower than the predetermined temperature (for example 20° C.), the liquid feeding switch means is shifted to RT enzyme solution (enzyme 1) 202 so as to introduce a predetermined amount of the RT solution 202 by driving the liquid feeding means 105. After the test material inlet nozzle 101 is removed from the container CB1, the temperature of the container holding means 10 is set at the predetermined temperature (for example, 42° C.), and the RT enzyme reaction for constructing cDNA from mRNA proceeds for a predetermined time (for example 30 to 60 minutes). After the temperature of the container holding means 10 is set at temperature equal to or lower than the predetermined temperature (for example, 20° C.), the liquid feeding switch means 220 is shifted to the waste liquid tank 210 so as to discharge reaction solution in container CB1 to the waste liquid tank 210 by driving the liquid feeding means 105. The liquid feeding switch means 220 is shifted to the TE solution 204 so as to introduce a predetermined amount of the TE solution 204 into the container CE1 by driving the liquid feeding means 105. The container holding means 10 is heated to a predetermined temperature (for example, 90° C.) by driving the solution temperature control means 30, at which temperature mRNA is hybridized. Then, the liquid feeding switch means 220 is shifted to container 206 for temporarily preserving mRNA, and dehybridized mRNA solution is moved to container 206 for temporarily preserving mRNA by driving the liquid feeding means 105.

Production of Replica Supports

Next, will be described a method for constructing replica supports by re-using dehybridized mRNA from the original cDNA library support produced by the above—described method. First, after removing the test material inlet/outlet nozzle 101 from container CB1, the nozzle 101 is moved to container CB2 containing a replica support (T2), temporarily preserved, inlet to the container CB2 by reversely driving the liquid feeding means 105. Then, steps described above for the production of the original support are repeated. However, the step for introducing the Total RNA solution 201 can be omitted. The liquid feeding switch means 220 is provided at a side of the reaction solution 203 of container CB2. The reaction solution is introduced into container CB2 by driving the liquid feeding means 105. After container CB2 has been maintained for a predetermined time (for example, 20 to 30 minutes) at a temperature equal to or lower than a predetermined temperature (for example, 20° C.), the liquid feeding switch means 220 is shifted to the RT enzyme solution (enzyme 1) 202 so as to introduced a predetermined amount of the solution by driving the liquid feeding means 105. The test material inlet/outlet nozzle is removed 101 from the container CB2, and the temperature of the container holding means 10 is maintained at a predetermined temperature (for example, about 42° C.) for a predetermined time (for example, 30 to 60 minutes). The a temperature of the container holding means 10 is set a temperature equal or lower than a room temperature (20° C.), and the liquid feeding switch means 220 is shifted to the waste liquid tank 210. The test material inlet/outlet nozzle 101 is inserted into container CB2, reaction solution in the container CB2 is discharged to the waste solution tank 210 by driving the liquid feeding means 105. The liquid feeding switch means 220 is shifted to the TE solution 204 so as to introduce a predetermined amount of the TE solution 204 into container CB2 by driving the liquid feeding means 105. Then, the liquid feeding switch means 220 is shifted to the waste liquid tank 210 so as to discharge the TE solution in container CB2 into the waste liquid tank. By repeating the above process several times (preferably at least 5 times), a first replica support is produced which is a duplicate of the original cDNA library support. The necessary numbers of replica supports are produced by repeating the cyclic operation for constructing the replica support the required number of times.

The device for constructing a DNA library support as shown in FIG. 2 comprises a liquid feeding means 105 for liquid feeding reaction solution etc. to a container, a liquid feeding switch means 220 for switching the liquid feeding of the reaction solution, a nozzle, a nozzle driving means 100 for driving a test material inlet/outlet nozzle 101 in a front-rear direction and left-right direction in a plane and an upper-lower direction, a container holding means 10 for holding a container in which a support is set, a container solution temperature control means 30 for heating or cooling the reaction liquid in the container, a test material container holding means 20 for holding containers in which test materials and test solutions for duplicating an immobilized DNA library support are set, respectively, and a test material container temperature control means 40 for controlling the test material container holding means at a predetermined temperature. It is preferred that at least 96 material test containers can be inserted into the container holding means 10 in view of connecting to a PCR device and/or a PCR product analysis device for subsequent operations. Preferably, the test material container holding means 20 contains at least four holes for a test material container in order to produce replica supports. It is preferred that the number of the test material holes provided at the test material container holding means 20 be at least 10 for subsequent connection to a PCR device and/or a PCR product analysis device. It is preferred that the container holding means 10 and the test material container holding means 20 be made of aluminum with good thermal conductivity in order to thermally control container liquid temperature control means 36 with Peltier element.

Production of Original Support of gDNA Library and its Replica Supports

Referring to FIGS. 2 and 5, the production of an original support and replica supports on which immobilized a gDNA library will be explained. The necessary number (T1~Tn) of supports (for example, 3 mm×3 mm×0.1 mm) of supports chemically modified with oligonucleotide sense portion having a restrictive enzyme portion are prepared. With respect to the original support, T1, oligo nucleotide (anti-sense portion) is hybridized and treated with restrictive enzyme so as to prepare a complete restrictive enzyme portion. The original support T1 is set in a container CB1. Replica supports T2–Tn are chemically modified with oligigonucleotide (sense portion) having restrictive enzyme portion are set in containers CB2–CBn. These containers are set in the solution holding means 10. With respect to a setting order, the container CB1 in which an original support T1 is set is inserted into a first inserting hole HT1 initially, and a second container and successive containers CB2–CBn, in which each replica support is set, is inserted in order. Reaction solution 303, including purified gDNA library solution 306 treated with restrictive enzyme, DNA ligase solution (enzyme 1) 305, DNA Polymerase solution (enzyme 2) 302 and nucleotide (dT, dA, dG, dC) 303 are set into a test material solution holding means 20 in which the temperature is maintained at a predetermined temperature (24° C.). TE solution for cleaning/eluting DNA 304 and a waste liquid tank 310 are provided. A capillary tube 330 for the respective solutions is connected to a liquid feeding switch means 220. It is preferred that the capillary tube 230 be a corrosion-resistant stainless tube for liquid chromatography.

The liquid feeding switch means 220 and the test material inlet/outlet nozzle 101 and others are connected to the front end of the capillary tube 230 through the liquid feeding means 105. A silicone tube 231 is preferred for this connection. A test material inlet/outlet nozzle 101 is moved to a location of the hole HT1 of the container holding means 10 so as to insert the nozzle 101 into the container CB1 in which the first support, T1, is set. The liquid feeding switch means 220 is shifted to the reaction solution 303 so as to inlet a predetermined amount (for example, 17 µL) of the reaction solution 303 by driving the liquid feeding means 105. The liquid feeding switch means 220 is shifted to the gDNA library solution 306 treated with restrictive enzyme so as to introduce a predetermined amount (for example, 2 µL) of the solution 306 by driving the liquid feeding means 105. After maintaining the container CB1 at a temperature equal to or lower than a predetermined temperature (for example, 20° C.) for a predetermined time (for example, 20 to 30 minutes), the liquid feeding switch means 220 is shifted to DNA ligase solution (enzyme 1) 305 so as to introduce a predetermined amount (for example, 1 µL) of the solution 305 into the container CB1 by driving the liquid feeding means 105. After removing the test material inlet/outlet nozzle 101 from container CB1, the temperature of the container holding means is maintained at a predetermined temperature (for example, 37° C.). After maintaining container CB1 at this temperature for a predetermined time (for example, 30 to 60 minutes), the gDNA library immobilized with DNA ligase is produced on the support T1. After maintaining the temperature of the container holding means 10 at a predetermined temperature (for example, equal to or less than 20° C.), the liquid feeding switch means 220 is shifted to the waste liquid tank 310 so as to insert the test material inlet/outlet nozzle 101 into container CB1 and discharge the reaction solution in container CB1 by driving the liquid feeding means 105. The liquid feeding switch 220 is shifted to the TE solution 304, a predetermined amount (for example, 500 µL) of the TE solution is introduced into container CB1 by driving the liquid feeding means 105. Then, the liquid feeding switch means 220 is shifted to the waste liquid tank 310 so as to discharge the TE solution in the container CB1. By repeating the process several times (for example, at least five times), the immobilized support T1 is cleaned. After the immobilized support T1 has been cleaned, the liquid feeding switch means 220 is shifted to the reaction solution 303 so as to introduce a predetermined amount (for example, 19 µL) of the reaction solution 303 into container CB1 by driving the liquid feeding means 105. By maintaining the temperature of the container holding means 10 at a predetermined temperature (for example, 90° C.), and maintaining the container CB1 at this temperature for a predetermined time (for example, 10 to 20 minutes), anti-sense portion is dehybridized from the immobilized gDNA library. Then, the liquid feeding switch means 220 is shifted to container 306 in which a gDNA library (anti-sense portion) is temporarily preserved so as to remove the gDNA library (anti-sense portion) solution from container CB1. This produces the first gDNA library (sense portion) support (original support).

Production of Replica Supports

The test material inlet/outlet nozzle 101 is removed from container CB1 and moved to the next container, CB2, in which a replica support (T2) is set so as to introduce the gDNA library (anti-sense portion) solution 306 temporarily preserved into container CB2. In order to produce a replica support, the above-described cyclic operation is repeated as necessary so as to produce the required number of replica supports. However, in the second embodiment described below, it is noted that DNA polymerase solution (enzyme 2) 302 is selected during a replica constructing process so as to introduce a predetermined amount (for example, 1 μL) of solution 302 into container CB2 by driving the liquid feeding means 105.

Embodiments

Embodiment 1

Figure 4:
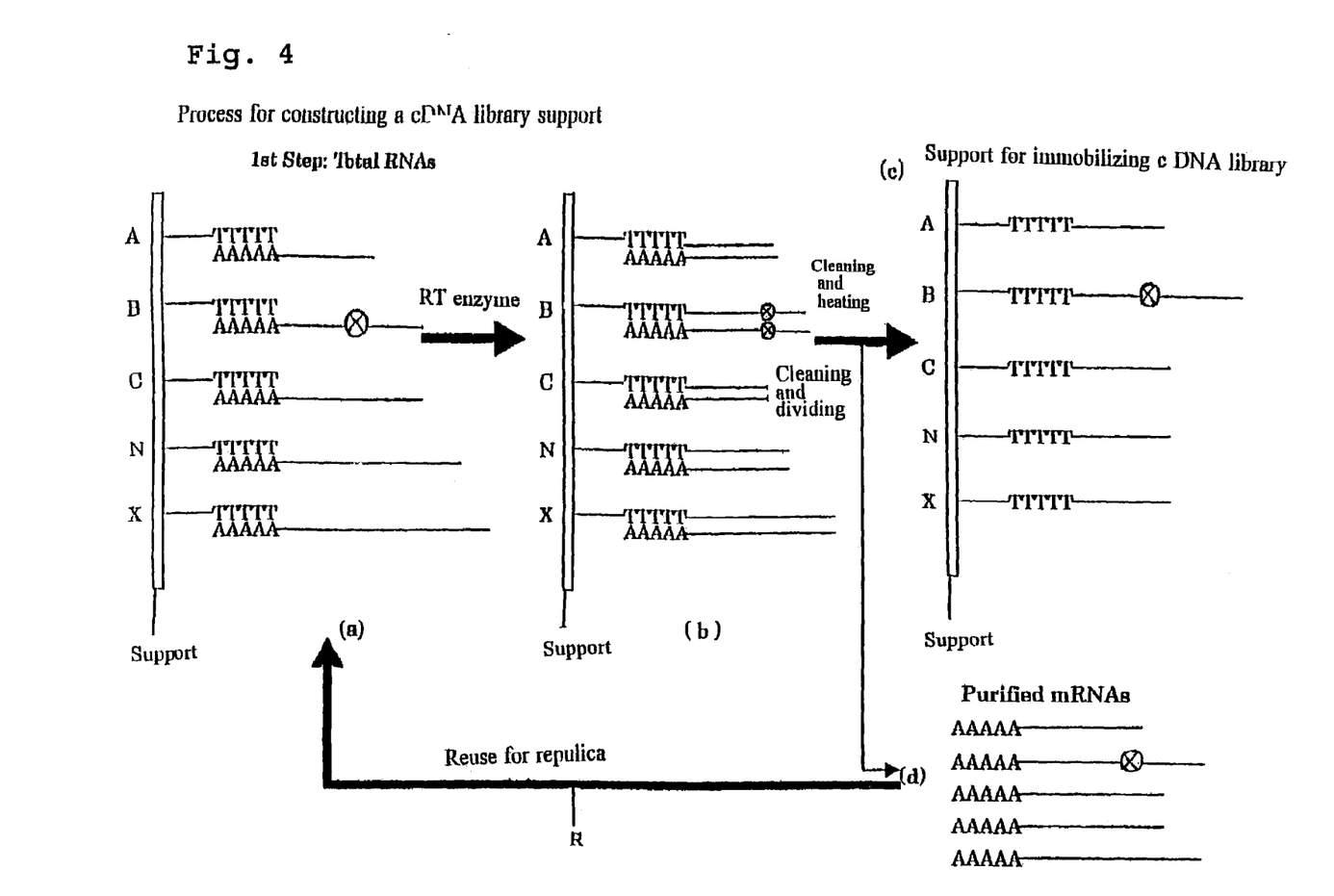
FIG. 4 is a schematic view for explaining a process for constructing a cDNA library support according to the present invention.

This embodiment, referring to FIGS. 1, 3, and 4, explains production of an original support immobilized a cDNA library, and production of replica supports. The test material is prepared by (1) breaking cells and tissues and purifying total RNA (see Step S1 in FIG. 3). For pre-treating a support immobilized with a cDNA library, a piece of rat liver tissue of about 5 mm×5 mm is homogenized in a test material kit (for example, ISOGEN sold by K.K. Nippon Gene) and the total RNA is purified in accordance with its protocol. Ten supports (T1~T1O) of 3 mm×3 mm×0.1 mm are chemically modified with oligo (dT)$_n$ (wherein n is from 15 to 30), as shown in Step 2 in FIG. 3. The supports T1–T10, immobilized with an amino group on their surfaces, are treated with activating dihydric carbonic solution. After being cleaned with ethanol and distilled water in that order, the supports are maintained in the oligo (dT)n solution for ten minuets. Each support is inserted into respective containers CB1~CB10, individually. The containers are set into the temperature controlling aluminum block 10. Reaction solution 203 including purified total RNA solution 201, RT enzyme solution 202 and nucleotide (dT, dA, dG, dC) are set into a low temperature test material aluminum block 20 in which the temperature is maintained at 4° C. TE solution (buffer liquid including tris-ethylene diamine tetraacetic acid) for cleaning DNA and the waste liquid tank 210 are provided at an exterior side of the low temperature test material aluminum block 20. The total RNA solution 201, the RT enzyme solution 202, the reaction solution 203, the TE solution 204, and the waste liquid tank 210 are connected to an automatic 8-way switching valve 220 through capillary tubes 230, respectively. A test material inlet/outlet capillary needle 101 is moved to the location of the inlet hole HT1 of the temperature control container aluminum block 10 so as to insert the capillary needle 101 into container CB1 in which the first support T1 (original support) is set. The automatic 8-way switching valve 220 is shifted to reaction solution 203 so as to introduce 17 μL of the reaction solution into container CB1 by driving a peristaltic pump 105. The automatic 8-way switching valve 220 is shifted to the total RNA solution 201, and 2 μL of solution 201 is pumped by the peristaltic pump 105. In order to hybridize oligo (dT) immobilized on a surface of the support and mRNA in the total RNA solution, the solutions are maintained at 20° C. for 20 minutes (see step S3 in FIGS. 3 and 4a). After this time, the automatic 8-ways switching valve 220 is shifted to RT enzyme solution 202 1 μL of the RT enzyme solution 202 by means of the peristaltic pump 105. After the test material inlet/outlet capillary needle 101 is removed from the container CB1, the container holding means 10 is maintained at 42° C. for 30 minutes so as to produce a cDNA library immobilized on support T1) by the RT enzyme (see a step S4 in FIGS. 3 and 4 b). After the container holding means is cooled to 10–20° C., the automatic 8-ways switching valve 220 is shifted to the waste liquid tank 210 to insert the test material inlet/outlet capillary needle 101 into container CB1. The reaction solution in container CB1 is discharged to the waste liquid tank 210 by driving the peristaltic pump 105. The automatic 8-way switching valve 220 is shifted to the TE solution 204. Five hundred μL of TE solution 204 is introduced into container CB1 by driving the peristaltic pump 105. Then the automatic 8-way switching valve 220 is shifted to the waste liquid tank 210 so as to discharge the TE solution in the container CB1 to the waste solution tank 210. By repeating this operation several times (at least five times), immobilized support T1 is cleaned (see step S5 in FIG. 3). After immobilized support T1 is cleaned, the automatic 8-way switching valve 220 is shifted to the reaction solution 203, 19 μL of reaction 203 is introduced into container CB1 by activating the peristaltic pump 105. Container holding means 10 is heated to 90° C., mRNA is dehybridized from the immobilized cDNA library after holding the support at this temperature for ten minutes (see step S6 in FIG. 3 and FIG. 4 d). Next, the automatic 8-way switching valve 220 is shifted to container 206 in which mRNA is temporarily preserved, dehybridized mRNA solution is eluted and removed from container CB1 and temporarily preserved in container 206 (see a step S7 in FIG. 3). In accordance with the above steps, the first cDNA library support, the original support on which a cDNA library is immobilized, is produced (see step S8 in FIGS. 3 and 4 c). After the test material inlet/outlet capillary needle 101 has been removed from container CB1, capillary needle 101 is moved to container CB2 in which a replica support, T2, is set. Replica support (T2) has been previously chemically modified. The automatic 8-way switching valve 220 is shifted to container 206 for temporarily preserving mRNA, and 19 μL of temporarily preserved mRNA is introduced to container CB2 by driving peristaltic pump 104 (see arrow R as shown in FIGS. 4d to 4a). In order to hybridize immobilized oligo (dT) and mRNA, container CB2 is maintained at 20° C. for 20 minutes. The automatic 8-way switching valve 220 is shifted to the RT enzyme solution 202 and 1 μL of RT enzyme solution 202 is introduce into container CB2 by driving the peristaltic pump 105 (see step S9 in FIG. 3). After the test material inlet/outlet capillary needle 101 has been removed from container CB2, the temperature of the container holding means 10 is controlled at 42° C. for 30 minutes so as to produce a cDNA library support immobilized on support T2 by RT enzyme (see a step S10 in FIGS. 3 and 4b). After the container holding means is cooled to 10 to 20° C., the automatic 8-way switching valve 220 is shifted to the waste liquid tank 210. The test material inlet/outlet capillary needle 101 is inserted into container CB2 so as to discharge the reaction solution in container CB2 to the waste liquid tank 210 by driving the peristaltic pump 105. The automatic 8-way switching valve 220 is shifted to the TE solution 204, 500 μL of TE solution 204 is introduced into container CB2 by driving the peristaltic pump 105. Then, the automatic 8-way switching valve 220 is shifted to the waste liquid tank 210 so as to discharge the TE solution in container CB2. By repeating the above operation five times, immobilized support T2 is cleaned (see step S11 in FIG. 3). After immobilized support T2 is cleaned, the automatic 8-way switching valve 220 is shifted to reaction solution 203. Then 19 µL of reaction 203 is introduced into container CB2 by driving the peristaltic pump 105. In the next step, the container holding means 10 is heated to 90° C. and maintained at that temperature for 10 minutes so as to dehybridize mRNA from the immobilized cDNA library see step S12 in FIG. 3). In the next step, the automatic 8-way switching valve 220 is shifted to the container 206 for temporarily preserving mRNA, dehybridized mRNA solution is separated and eluted from container CB2 by driving the peristaltic pump 105 (see FIG. 4d) and temporarily preserved in container 206 (see step S13 in FIG. 3). In accordance with the above steps, a replica cDNA library support (replica support) is produced (see step S14 in FIGS. 3 and 4 (c).

With respect to the containers CB3–CB10 in which supports T3–T1O are inserted, respectively, a similar process is conducted. By repeating the above steps S9 through S14 in order, eight replica supports are produced. By utilizing supports T1–T1O immobilized with a cDNA library of rat liver tissue, a gene is amplified by a PCR device with respect to 18S rRNA. AN electrophoresis device is used to confirm that the cDNA Library is immobilized. Thus, it can be confirmed that the original support T1 and the replica supports T2–T1O are produced as normal cDNA library supports.

Embodiment 2

Figure 6:
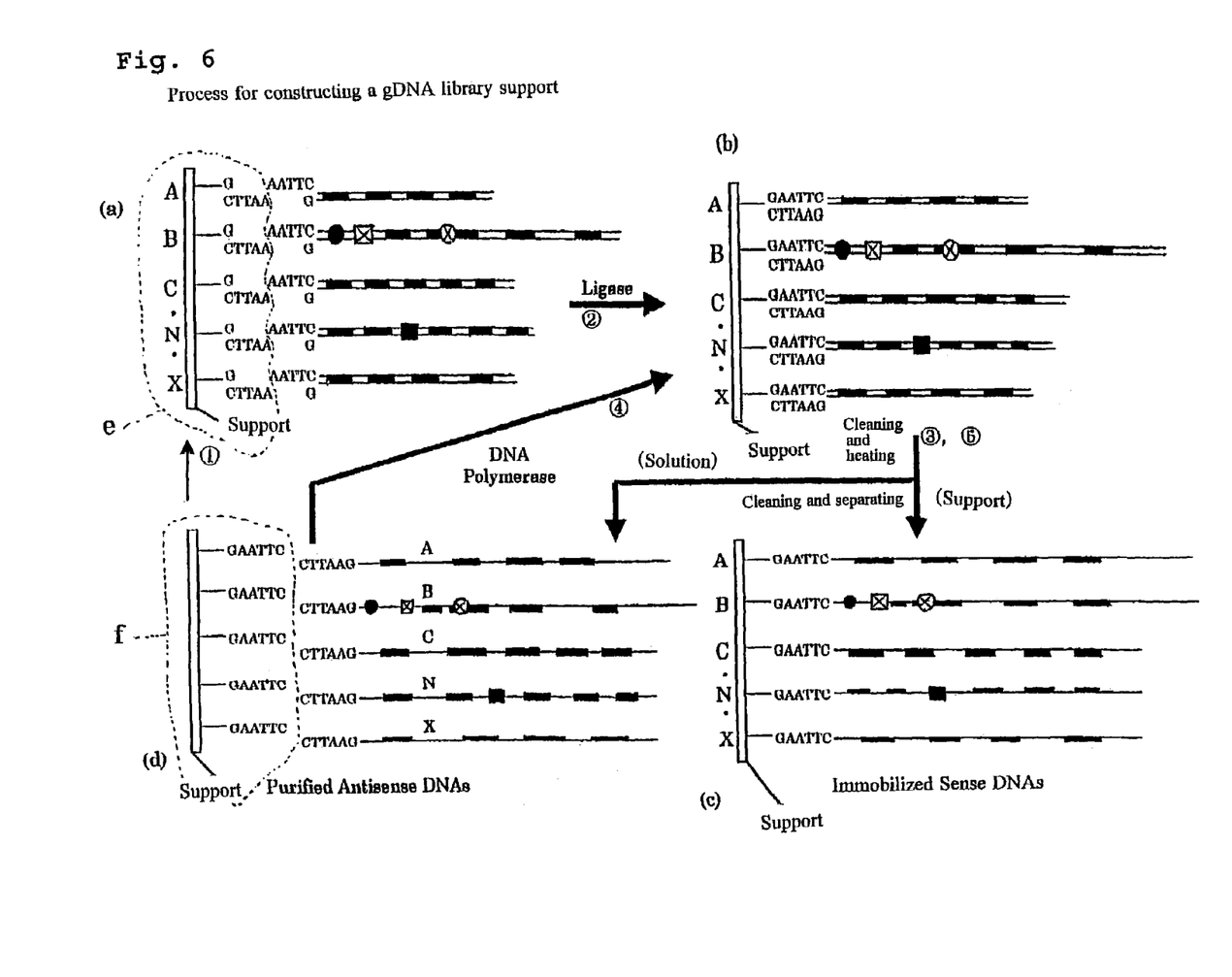
FIG. 6 is a schematic view for showing a process for constructing a gDNA library support according to the present invention.
Figure 7:
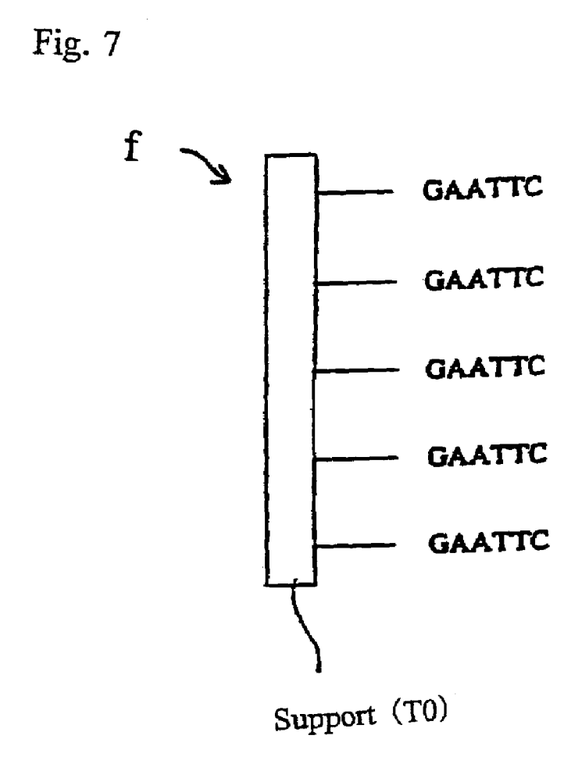
FIG. 7 is an enlarged view of support f.
Figure 8:
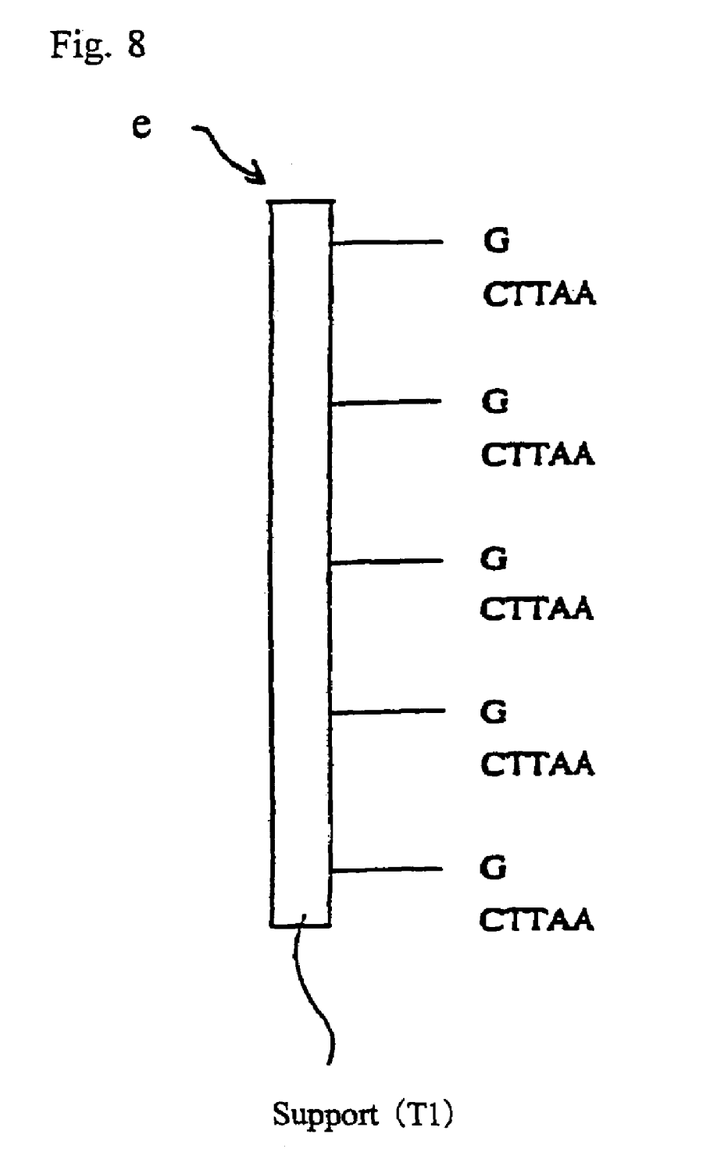
FIG. 8 is an enlarged view of support e.

Production of an original support on which is immobilized with a gDNA library and its replica supports are explained with reference to FIGS. 2, 5,6, and 7. Test materials are prepared by (1) breaking cells and tissues and (2) purifying and treating gDNA with restrictive enzyme (see step S21 in FIG. 5). Ten supports chemically modified with a sense portion of oligo nucleotide a having base sequence of a target restrictive enzyme portion are prepared. The size of the support is about 3 mm×3 mm×0.1 mm (see step S22 in FIG. 5). A concept of the support is shown as support f surrounded with a broken line in FIG. 6d. FIG. 7 is an enlarged view of the portion. By using one chemically modified support, an anti-sense portion of the oligo nucleotide is hybridized. The support is treated with restrictive enzyme so as to produce one support, T1, having a complete restrictive enzyme cut portion (see step S23 in FIG. 5 and an arrow (1) in FIGS. 6 d to 6a). A concept of the support is shown as a support e surrounded with a broken line in FIG. 6 a. FIG. 8 is an enlarged view of this portion.

Support TI is inserted into container CB1, and nine supports chemically modified with a sense portion of oligonucleotide having the restrictive enzyme portion are introduced into the container holding means 10. As shown in FIG. 2, the reaction solution 303, including purified gDNA library solution 306 treated with restrictive enzyme, DNA solution (enzyme 1) 305, DNA Polymerase solution (enzyme 2) 302 and nucleotide (dT, dA, dG, dC) are set into a low temperature test material aluminum block 20 in which the temperature is controlled at 4° C. TE solution 304 for cleaning/eluting DNA and a waste liquid tank 310 are provided at an exterior side of the low temperature test material aluminum block 20. As shown in FIG. 2, reaction solution 303 including the GDNA (genomic DNA) library solution 306, the DNA Ligase solution (enzyme 1) 305, the DNA polymerase solution (enzyme solution 2) 302 and nucleotide (dT, dA, dG, dC), TE solution 304 for cleaning/eluting DNA and the waste liquid 310 are connected to an automatic 8-way switching valve 220 through a capillary tube 230, respectively. The test material inlet/outlet capillary needle 101 is moved to a location of the hole HT1 of the temperature control container aluminum block 10 so as to insert the capillary needle 101 into the container CB1 in which the first support T1 (original support) is set. The automatic 8-way switching valve 220 is shifted to the reaction solution 303, and 17 µL of reaction solution 303 is introduce into container CB1 by driving the peristaltic pump 105. The automatic 8-way switching valve 220 is shifted to the gDNA library solution 306 treated with restrictive enzyme, 2 µL of this solution is pumped by the peristaltic pump. After the has been maintained at 20° C. for 20 minutes, the automatic 8-way switching valve 220 is shifted to DNA ligase solution (enzyme 1) 305 so as to introduce 1 µL of solution 305 to the container CB1 by driving the peristaltic pump 105. After removing the test material inlet/outlet capillary needle 101 from the container CBI, the temperature of the container holding means 10 is maintained at 37° C. for 30 minutes so as to produce the gDNA library immobilized by DNA ligase on the support T1 (see step S25 in FIG. 5 and an arrow 2 in FIGS. 6a and 6b). After the container holding means is cooled to 10 to 20° C., the automatic 8-way switching valve 220 is shifted to the waste liquid tank 310 so as to discharge the reaction solution in the CB1 by driving the peristaltic pump 105. The automatic 8-way switching valve 220 is shifted to the TE solution 304 and 500 µL of TE solution is introduced into container CB1 by driving the peristaltic pump 105. By repeating these steps five times or more, support T1 is cleaned (see step S26 in FIG. 5). After cleansing the support T1, the automatic 8-way switching valve 220 is shifted to the reaction solution 303. Nineteen µL of reaction solution is introduced into container CB1 by driving the peristaltic pump 105. The temperature control container aluminum block 10 is heated to 90° C. and maintained for 10 minutes, an anti-sense portion is dehybridized from a double stranded sense portion and the anti-sense portion of the immobilized DNA library (see step S27 in FIG. 5 and arrow (3) in FIGS. 6b and 6c). The automatic 8-way switching valve 220 is shifted to a container 306 for temporary preservation so as to elute the anti-sense portion of the gDNA library solution from container CB1 by driving the peristaltic pump 105 (see step S29 in FIG. 5 and arrow in FIGS. 6b and 6d). The sense portion is only immobilized on support T1. Thus, the first support, that is, single stranded gDNA library support TI, original support, is produced (see step S28 in FIGS. 5 and 6 c. After removing the test material inlet/outlet capillary needle 101 from the container CB1, the capillary needle 101 is moved to container CB2 which holds the support T2. The reaction solution including nucleotide is added to container CB2, which is maintained at 20° C. The gDNA library solution 306 including only anti-sense portion temporarily preserved is introduced into container CB2 and maintained for 20 minutes (see step S30 in FIG. 5). In the next step, DNA polymerase is added, container CB2 is heated to 37° C. and maintained at his temperature for one hour. As a result, a double stranded gDNA library, of which a sense portion is immobilized on the support T2, is produced (see step S31 and arrow (4) in FIGS. 6d and 6 b). Container CB2 in which the support T2 is immobilized with the above double stranded gDNA library is maintained at 20° C. After shifting the automatic 8-way switching valve 220 to the waste liquid tank 310, the test material inlet/outlet capillary needle 101 is introduced into container CB2. The reaction solution in container CB2 is discharged by driving the peristaltic pump 105. The automatic 8-way switching valve 220 is then shifted to the waste liquid tank 310, and the TE solution in the container CB2 is discharged. By repeating the above steps at least five times, support T2 is cleaned (see a step S32 in FIG. 5). After support T2 has been cleaned, the automatic 8-way switching valve 220 is shifted to reaction solution to 303 to introduce 19 µL of this reaction solution into container CB2 by driving the peristaltic pump 105. The aluminum block 10 is heated to 90° C. and maintained at that temperature for ten minutes to dehybridize the anti-sense portion from immobilized gDNA library with double stranded sense portion and the anti-sense portion (see step S33 in FIG. 5 and arrow (5) in FIGS. 6b to 6c). The automatic 8-way switching valve 220 is shifted to a container for temporarily preservation so as to outlet the anti-sense portion of gDNA library solution from the container CB2 (see step S35 in FIG. 5 and an arrow in FIGS. 6b to 6d. A second single stranded gDNA library support, that is, a replica support T2 on which a sense portion is immobilized, is produced (see step S34 in FIGS. 5 and 6c). By repeating the above steps, a double stranded gDNA library is immobilized on a support. An anti-sense portion is dehybridized from the double stranded immobilized gDNA library so as to produce the remaining number (T3–T1O) of single stranded gDNA library supports (replica supports). That is, the process including steps as shown in FIGS. 6b and 6d is repeated so that any number of supports on which the same single stranded gDNA library is immobilized can be produced.

The present invention produces a support immobilized with cDNA library from mRNA and a gDNA library treated with a restrictive enzyme of gDNA. Although it is impossible to produce replica supports duplicated from DNA library solution in the conventional art, the required number (until mRNA and gDNA are chemically or physically denatured) of replica supports can be produced by the method of the present invention. An immobilized DNA library support and its replica supports can be produced by collecting micro amounts of gene material from cultured cells or tissues of an important object to be detected. Various kinds of gene research and detection can be effected using the same kinds of test materials. By using the immobilized DNA library support and its replica supports, developing a new gene diagnosis technology can be more cheaply and easily than by using conventional techniques. If blood is collected from a patient or tissue is collected in a medical procedure at one time for gene diagnosis, the collected blood or tissue can be easily re-used with respect to preventive medical research, since a plurality of immobilized DNA library supports can be produced over a long period of time. The process of the present invention makes it possible to perform many diagnoses on a patient from sample, reducing mental and/or economic stress on a patient.

What is claimed is:

1. A method for immobilizing a cDNA library on an original support and at least one replica support comprising:
   a. immobilizing an amino group on the surface of the original support
   b. contacting the original support with oligo (dT)n to immobilize the oligo (dT)n onto the original support, wherein n is from 15 to 30;
   c. treating the original support with a reaction solution comprising total RNA, reverse transcriptase, and nucleotides to construct cDNA from mRNA;
   d. maintaining the original support in contact with the reaction solution at 20° C. to hybridize oligo (dT)n on the original support and mRNA in the total RNA solution;
   e. treating the original support with reverse transcriptase solution and maintaining the original support in contact with reverse transcriptase to produce a cDNA library immobilized on the original support;
   f. cleaning the original support and heating the original support to dehybridize mRNA from the original support; and
   g. repeating steps b–f using a replica support in place of the original support in order to produce a replica cDNA library immobilized on the support.

2. The method according to claim 1 wherein dehybridized mRNA solution is temporarily preserved.

3. The method according to claim 2 wherein the mRNA that is temporarily stored is used in the reaction solution.

4. A method for immobilizing a gDNA library on an original support and at least one replica support comprising:
   h. immobilizing an amino group on the surface of the original
   i. contacting the original support with a sense portion of oligo nucleotide having the base sequence of a target restrictive enzyme;
   j. treating the original support with restrictive enzyme to produce a support having a complete restrictive enzyme cut portion
   k. treating the original support with a reaction solution comprising purified gDNA library solution treated with restrictive enzyme, DNA ligase solution, DNA polymerase solution, and nucleotides;
   l. maintaining the original support in contact with the reaction solution at 20° C. to produce the gDNA library immobilized by DNA ligase on the support;
   m. cleaning the original support and heating the original support to dehybridize mRNA from the original support;
   n. heating the original support to dehybridize an anti-sense portion from a double stranded sense portion and eluting the anti-sense portion of the gDNA library from the support; and
   o. repeating steps b–f using a replica support in place of the original support in order to produce a replica gDNA library immobilized on the support.

* * * * *